United States Patent [19]

Cricchio

[11] 4,271,155
[45] Jun. 2, 1981

[54] WATER SOLUBLE HYDRAZONES OF 3-FORMYLRIFAMYCIN SV, ANTIBACTERIAL COMPOSITIONS THEREOF AND METHOD OF USE THEREOF

[75] Inventor: Renato Cricchio, Varese, Italy

[73] Assignee: Gruppo Lepetit S.p.A., Milan, Italy

[21] Appl. No.: 160,799

[22] Filed: Jun. 19, 1980

[30] Foreign Application Priority Data

Jun. 28, 1979 [GB] United Kingdom ............... 22461/79

[51] Int. Cl.$^3$ .................. C07D 491/06; A61K 31/395
[52] U.S. Cl. ............................. 424/200; 260/239.3 P; 542/403
[58] Field of Search ................. 260/239.3 P; 424/200; 542/403

[56] References Cited

U.S. PATENT DOCUMENTS

| 3,862,934 | 1/1975 | Cricchio et al. | 260/239.3 P |
|---|---|---|---|
| 3,865,812 | 2/1975 | Cricchio et al. | 260/239.3 P |
| 4,002,752 | 1/1975 | Cricchio et al. | 260/239.3 P |
| 4,002,754 | 1/1975 | Cricchio et al. | 260/239.3 P |
| 4,005,076 | 1/1977 | Cricchio et al. | 260/239.3 P |
| 4,193,920 | 3/1980 | Konstantinova et al. | 260/239.3 P |

Primary Examiner—Robert T. Bond
Attorney, Agent, or Firm—Maynard R. Johnson

[57] ABSTRACT

The invention relates to new water soluble 3-formylrifamycin SV hydrazones wherein the hydrazone moiety contains a phosphonoxy lower alkyl radical which imparts water solubility. The compositions containing said rifamycin derivatives are also an object of this invention. The new rifamycin derivatives and their pharmaceutical compositions are particularly suitable for parenteral administration.

6 Claims, No Drawings

WATER SOLUBLE HYDRAZONES OF 3-FORMYLRIFAMYCIN SV, ANTIBACTERIAL COMPOSITIONS THEREOF AND METHOD OF USE THEREOF

This invention relates to new water soluble rifamycin derivatives. More particularly this invention relates to water soluble hydrazones of 3-formylrifamycin SV of the general formula:

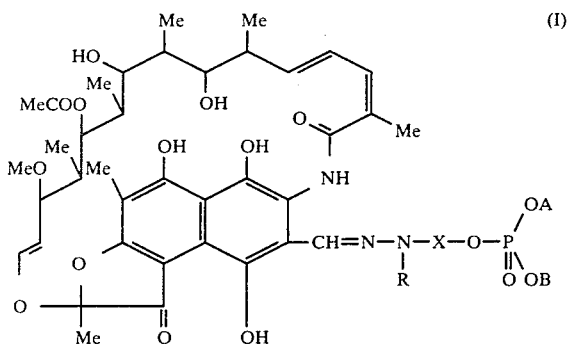

wherein
R is hydrogen, lower alkyl or a group

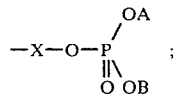

X is an alkylene radical of 1 to 5 carbon atoms;
A is hydrogen, lower alkyl, phenyl, benzyl or a pharmaceutically acceptable cation;
B is hydrogen or a pharmaceutically acceptable cation.

In the description and in the claims, the term "lower alkyl" represents a straight or branched alkyl radical of 1 to 5 carbon atoms; representative examples of said "lower alkyl" group are for instance, methyl, ethyl, propyl, isopropyl, isobutyl, pentyl and neopentyl. The term alkylene radical of 1 to 5 carbon atoms identifies straight or branched saturated hydrocarbon divalent radicals of 1 to 5 carbon atoms such as methylene, ethylidene, ethylene, propylene, ethylethylene, trimethylene, tetramethylene, and pentamethylene. The term "pharmaceutically acceptable cations" means cations derived from inorganic or organic bases which form water soluble salts with the phosphoric acid moiety of the molecule and do not cause any adverse physiological effect when administered to an animal at dosages consistent with good pharmacological activity. Said cations are preferably derived from bases such as sodium hydroxide, potassium hydroxide, calcium hydroxide, magnesium carbonate, ammonia, primary secondary and tertiary amines such as ethanolamine, diethanolamine, diethylamine, triethylamine, dimethylamine, triethanolamine; N,N'-dibenzyl ethylendiamine.

A second object of this application is a process for the manufacture of the compounds of formula I.

A further object of this application is the use of the new water soluble rifamycin derivatives as antibacterial agents and the pharmaceutical compositions suitable for the administration thereof, according to such use.

The compounds of this invention besides preserving the remarkable antibacterial properties of the rifamycins antibiotics having a 3-iminomethyl moiety, show high solubility in aqueous vehicles and good local tolerability. Because of these properties, the novel rifamycins derivatives of this invention are very suitable as antibacterial agents for parenteral administration.

The new rifamycins of formula I are in fact completely soluble in water or in mixture of water with other pharmaceutically acceptable solvents mixable with water. Useful solvents which can be admixed with water are for instance the polyhydric aliphatic alcohols such as ethylene glycol, propylene glycol, glycerine and mixtures thereof. These solutions can be added with buffers to maintain the pH range at a physiological value. For instance, ten grams of the compound of formula I wherein R is methyl, X is

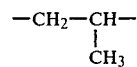

are completely soluble in 100 ml of water buffered at pH 7.38 (phosphate buffer). The corresponding compound wherein A and B are both the sodium cation is even more soluble; in fact 100 ml of water can dissolve about fifty grams of said compound.

When used for parenteral administration the solutions containing the new rifamycin derivatives can also be added with other ingredients to provide isotonicity compatible with the body isotonicity. Besides, it may be desirable to incorporate in said solutions a local anesthetic, as it is well known to those skilled in the art.

Although the aqueous solutions of the new rifamycin derivatives of formula I are particularly suitable for parenteral administration, they can be advantageously utilized also for administration through the alimentary canal, for instance as pediatric droplets, or for external applications such as solutions, mouth-washes and collyria.

When used for parenteral or oral administration the new rifamycin derivatives of this invention are easily adsorbed from the carrier solution and rapidly transferred into the infected body districts through the circulatory system.

The new rifamycin derivatives are prepared according to commonly known chemical reactions involving condensation of a suitable rifamycin substrate with a phosphorilated hydrazine. Suitable rifamycin substrates are for instance rifamycin SV substituted in the position 3 with a formyl group or a chemical equivalent thereof, such as a Schiff base or an acetal. More particularly, according to this process, 3-formylrifamycin SV, or a corresponding acetal or Schiff base, is contacted in a suitable solvent system with a hydrazine alkyl phosphoric acid derivative of the formula

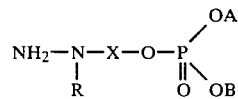

wherein R, X, A and B have the same meaning as before. Other rifamycin derivatives which are known to behave in the same way as 3-formylrifamycin toward hydrazines may also be employed as rifamycin substrates for the condensation with the phosphorylated hydrazines. For instance, the 1,3-oxazine(5,6-c)rifamycin derivatives utilized as starting materials in the process of U.K. Patent No. 1,454,802 and the pyrimido-rifamycins starting compound of the process described in the Japanese Patent Application Publication J5 2087198 (Derwent C.P.I. 62189 Y) are employable as starting materials in the process described here for the manufacture of the compounds of this invention.

According to a preferred embodiment of the process for the manufacture of the compound of this invention, the rifamycin substrate is dissolved in an organic solvent mixable with water such as acetone, a lower alkanol, tetrahydrofuran, dioxane, and dimethylformamide, and this solution is contacted with the appropriate hydrazinoalkylphosphoric acid derivative preferably dissolved in water and in excess over the molecular proportion stoichiometrically required. The mixture is stirred at the room temperature until TLC assays show that the reaction is completed. After further addition of water, the reaction mixture is acidified to a pH value of 2 to 3 and then is extracted with a water immiscible organic solvent. The reaction product is recovered from the organic layer by concentration. The salts of the compounds of formula I wherein A and B are both hydrogen, that is, those compounds of formula I wherein A and/or B represent a pharmaceutically acceptable cation are prepared by adding the desired base to a solution of the corresponding acid in an aqueous solvent and then evaporating the mixture to dryness.

The hydrazinoalkylphosphoric acid derivatives employed for the manufacture of the compounds of this invention may be prepared according to the procedure described for the hydrazinoethylphosphoric acid by J. Rabinowitz et al. in Helvetica Chimica Acta, 52, 250 (1969). The hydroxyalkyl hydrazine derivatives which are employed for the manufacture of the hydrazinoalkylphosphoric acids may be prepared according to literature methods by direct alkylation of hydrazine with hydroxyalkyl halides or sulfates. When X stands for an ethylene or alkyl substituted ethylene radical, a preferred method for preparing the $\beta$-hydroxyalkyl hydrazines is that described by D. L. Trepanier et al. in J. Org. Chem. 29, 673 (1964).

The antibacterial activity of the new compounds may be demonstrated in representative experiments with two sets of mice infected respectively with *Staphylococcus aureus* Tour and *Escherichia coli* strains. The values of the ED$_{50}$ of the compounds of examples 2, 3 and 4 against the two microbial strains and the toxicity (LD$_{50}$) of the compounds are reported in the following Table

| Compound of Example No. | ED$_{50}$ (mg/kg) s.c. | | LD$_{50}$ (mg/kg) in mice | |
|---|---|---|---|---|
| | S. aureus Tour | E. coli | i.v. | i.p. |
| 2 | 0.812 | 98.5 | 665 | 770 |
| 3 | 0.812 | 130 | 525 | >500 |
| 4 | 1.51 | 106 | 507 | 592 |

For the use as antibacterial agents, the compounds of this invention may be administered to patients in amounts which may vary depending on several factors such as the severity of the disease, the period of administration and the method of administration.

In general a daily effective dosage range for parenteral and oral administration is from about 0.5 mg to about 50 mg per kilogram of body weight, with a daily dosage range from 1 to 20 mg per kilogram of body weight being preferred.

The following examples will serve to illustrate the method of manufacture of the novel compounds without limiting the scope of the invention.

EXAMPLE 1

3-[[[2-(Phosphonoxy)ethyl]hydrazono]methyl]rifamycin SV. (I: R=H; X=—CH$_2$—CH$_2$—; A=B=H)

To a solution of 7.25 g of 3-formylrifamycin SV in 50 ml of acetone are added 4 g of 2-hydrazinoethanol phosphate (prepared according to J. Rabinowitz et al. Helv. Chim. Acta, 52, 250,1969) dissolved in 200 ml of water. The mixture is stirred for four hours at room temperature and then is diluted with 250 ml of water and extracted twice with 100 ml of butanol to eliminate the side products formed. The aqueous phase is acidified to pH 2.5 and than extracted with three portions (each of 200 ml) of ethyl acetate; the organic extracts are combined and anhydrified over sodium solfate. Evaporation of the ethyl acetate solution under vacuum yields 4 g of the product to the title, a solid which decomposes on heating at 200° C.

Elemental analysis for C$_{40}$H$_{54}$N$_3$O$_{16}$P—Calculated %: C=55.61; H=6.30; N=4.86; P=3.58. Found %: C=53.94; H=6.27; N=4.98; P=3.60.

U.V. spectrum in pH 7.38 buffer

| $\lambda$ max | $E_{1cm}^{1\%}$ |
|---|---|
| 230 | 330 |
| 330 | 251 |
| 470 | 146 |

The I.R. and N.M.R. data are in agreement with the assigned structure.

EXAMPLE 2

3-[[[2-(Phosphonoxy)propyl]methylhydrazino]methyl]-rifamycin SV. (I: R=CH$_3$; X=—CH$_2$——CH(CH$_3$)—; A=B=H)

To a solution of 7 g of 3-formylrifamycin SV in 250 ml of 50% aqueous acetone are added 12 g of 1-(1-methylhydrazino)-2-propanol phosphate (the product is prepared according to the same procedure described for the corresponding ethyl derivative in the paper published J. Rabinowitz et al. in Helvetica Chimica Acta, 52, 250, 1969 and is used without any further purification).

The mixture is stirred at the room temperature for 4 hours; then it is diluted with 250 ml of water and extracted twice with 100 ml of butanol. The aqueous phase is acidified at pH 2.7 and then extracted with three portions of ethyl acetate (each of 200 ml). The combined organic layers are dryed over sodium sulfate and then concentrated under vacuum to yield 3.5 of the product of the title, a solid which decomposes on heating at 170° C.

Elemental analysis for C$_{42}$H$_{58}$N$_3$O$_{16}$P—Calculated %: C=56.55; H=6.55; N=4.71; P=3.47. Found %: C=55.30; H=6.55; N=5.07; P=3.90.

U.V. spectrum in pH 7.38 buffer

| $\lambda$ max | $E_{1cm}^{1\%}$ |
|---|---|
| 338 | 272 |
| 475 | 163 |

The I.R. and N.M.R. data are in agreement with the assigned structure.

The product (100 mg) is converted to the corresponding di-sodium salt by dissolving in 50% methanol (10 ml) containing two equivalent amounts of sodium methoxide and evaporating the solution to dryness under vacuum.

EXAMPLE 3

3-[[[2-(Phosphonoxy)butyl]methylhydrazono]methyl]-rifamycin SV. (I: R=CH$_3$; X=—CH$_2$——CH(C$_2$H$_5$)—; A=B=H)

The product is obtained from 3-formylrifamycin SV (7 g) and 1-(1-methylhydrazino)-2-butanol (11 g) according to the procedure described in example 2. Yield 2.8 g. The product decomposes at 160° C.

Elemental analysis for C$_{43}$H$_{60}$N$_3$O$_{16}$P—Calculated %: C=57.01; H=6.67; N=4.64; P=3.42. Found %: C=55.95; H=6.77; N=5.01; P=3.56.

U.V. spectrum in pH 7.38 buffer

| λ max | $E_{1cm}^{1\%}$ |
|-------|-----------------|
| 232   | 277             |
| 339   | 251             |
| 475   | 148             |

The I.R. and N.M.R. data are in agreement with the assigned structure.

EXAMPLE 4

3-[[[2-(Phosphonoxy)ethyl]methylhydrazono]methyl]-rifamycin SV. (I: R=CH$_3$; X=—CH$_2$—CH$_2$—; A=B=H)

The product is obtained from 3-formylrifamycin SV (14 g) and 2-(1-methylhydrazino)ethanol (10 g) according to the procedure described in example 1. Yield 8.5 g. The product decomposes at 150° C.

Elemental analysis for C$_{40}$H$_{56}$N$_3$O$_{16}$P—Calculated %: C=56.48; H=6.52; N=4.85; P=3.57. Found %: C=54.76; H=6.33; N=4.92; P=3.54.

U.V. spectrum in pH 7.38 buffer

| λ max | $E_{1cm}^{1\%}$ |
|-------|-----------------|
| 235   | 341             |
| 336   | 268             |
| 470   | 154             |

The I.R. and N.M.R. data are in agreement with the assigned structure.

I claim:

1. A rifamycin compound of the formula (I)

[Structural formula of rifamycin compound with substituent —CH=N—N(R)—X—O—P(OA)(OB)=O]

wherein

R is hydrogen, lower alkyl or $$-X-O-P\underset{O}{\overset{OA}{\underset{\|}{\diagup}}}_{OB}\;;$$

X is alkylene of 1 to 5 carbon atoms;
A is hydrogen, lower alkyl, phenyl, benzyl or a pharmaceutically acceptable cation;
B is hydrogen or a pharmaceutically acceptable cation.

2. A compound of claim 1 wherein R is hydrogen or methyl; X is ethylene, methylethylene or ethyletylene A and B are each independently hydrogen or sodium.

3. An antibacterial composition comprising from about 0.01 percent by weight to about 50 percent by weight of a compound of claim 1 dissolved in a pharmaceutical liquid vehicle.

4. An antibacterial composition as in claim 3 wherein the composition is in dosage unit form adapted for parenteral administration as an antibacterial agent and wherein the composition contains from about 50 to about 500 mg of a compound of claim 1 per unit.

5. A method of preventing or combatting bacterial infections in animals which comprises administering to animals an antibacterially effective amount of a compound of claim 1.

6. The method of claim 5 wherein the compound is administered by the parenteral route.

* * * * *